(12) United States Patent
Nazzaro et al.

(10) Patent No.: US 10,684,271 B2
(45) Date of Patent: Jun. 16, 2020

(54) DIAGNOSTIC MEDICAL DEVICE AND METHODS OF USE THEREOF

(71) Applicant: Insulet Corporation, Billerica, MA (US)

(72) Inventors: David Nazzaro, Groveland, MA (US);
John Bussiere, Littleton, MA (US);
Jason B. O'Connor, Acton, MA (US);
John D. D'Arco, Wilmington, MA (US)

(73) Assignee: INSULET CORPORATION, Acton, MA (US)

( * ) Notice: Subject to any disclaimer, the term of this patent is extended or adjusted under 35 U.S.C. 154(b) by 661 days.

(21) Appl. No.: 15/009,979

(22) Filed: Jan. 29, 2016

(65) Prior Publication Data
US 2017/0219555 A1 Aug. 3, 2017

(51) Int. Cl.
*G01N 33/487* (2006.01)
*G01N 33/49* (2006.01)

(52) U.S. Cl.
CPC ......... *G01N 33/4875* (2013.01); *G01N 33/49* (2013.01)

(58) Field of Classification Search
CPC ............................ G01N 33/4875; G01N 33/49
USPC ...................................................... 73/61.59
See application file for complete search history.

(56) References Cited

U.S. PATENT DOCUMENTS

| 5,232,668 | A | * | 8/1993 | Grant ................... G01N 21/474 |
| | | | | 422/429 |
| 5,995,236 | A | | 11/1999 | Roth et al. |
| 6,514,460 | B1 | | 2/2003 | Fendrock |
| 7,731,900 | B2 | | 6/2010 | Haar et al. |
| 7,820,105 | B2 | | 10/2010 | Arbogast et al. |
| 7,842,241 | B2 | | 11/2010 | Arbogast et al. |
| 7,846,385 | B2 | | 12/2010 | Arbogast et al. |
| 7,846,386 | B2 | | 12/2010 | Arbogast et al. |
| 7,846,387 | B2 | | 12/2010 | Arbogast et al. |
| 7,846,388 | B2 | | 12/2010 | Arbogast et al. |
| 7,867,446 | B2 | | 1/2011 | Arbogast et al. |
| 7,897,107 | B2 | | 3/2011 | Abrogast et al. |
| 7,914,742 | B2 | | 3/2011 | Arbogast et al. |
| 8,080,205 | B2 | | 12/2011 | Arbogast et al. |
| 8,431,408 | B2 | | 4/2013 | Lewis et al. |
| 8,465,977 | B2 | | 6/2013 | Joseph et al. |
| 8,765,482 | B2 | | 7/2014 | Joseph et al. |
| 8,894,262 | B2 | | 11/2014 | Celentano et al. |
| 2005/0009126 | A1 | * | 1/2005 | Andrews ................... C12Q 1/54 |
| | | | | 435/14 |
| 2005/0125162 | A1 | | 6/2005 | Hajizadeh et al. |
| 2005/0201897 | A1 | | 9/2005 | Zimmer et al. |
| 2005/0232815 | A1 | | 10/2005 | Ruhl et al. |

(Continued)

*Primary Examiner* — Marrit Eyassu

(57) ABSTRACT

A medical device to test bodily fluid, the device comprising a light emitting source, the light emitting source arranged to emit light inside the medical device; a test strip port, the test strip port comprising a test strip port receptacle to receive a test strip; and the light emitting source and the test strip port arranged such that, when the light emitting source emits light, at least a portion of the light emitted from the light emitting source is redirected inside the medical device to provide redirected light inside the medical device, and at least a portion of the redirected light lights the test strip port from inside the medical device in a manner than the redirected light is visible outside the test strip port.

17 Claims, 9 Drawing Sheets

(56) References Cited

U.S. PATENT DOCUMENTS

| | | | |
|---|---|---|---|
| 2010/0317951 A1* | 12/2010 | Rutkowski | A61B 5/14532 600/365 |
| 2011/0193704 A1* | 8/2011 | Harper | A61B 5/14532 340/573.1 |
| 2011/0289497 A1* | 11/2011 | Kiaie | G06F 8/65 717/171 |
| 2012/0095316 A1* | 4/2012 | Lewis | A61B 5/14532 600/365 |
| 2012/0201048 A1 | 8/2012 | Prais | |
| 2014/0131199 A1* | 5/2014 | Simmons | A61B 5/14532 204/403.02 |
| 2014/0254170 A1* | 9/2014 | Celentano | F21V 33/0068 362/297 |
| 2015/0283335 A1* | 10/2015 | Lin | A61M 5/5086 604/111 |
| 2015/0338349 A1* | 11/2015 | Carter | F21V 33/0068 436/95 |
| 2017/0234858 A1* | 8/2017 | Depa | A61B 5/6898 436/165 |

* cited by examiner

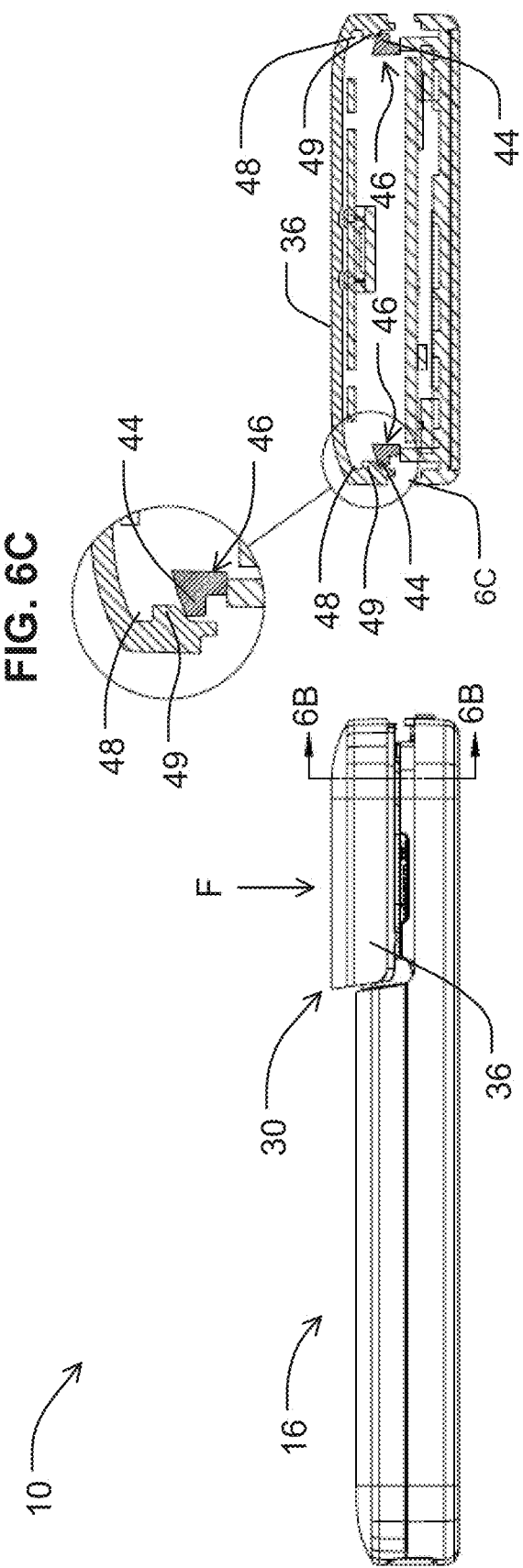

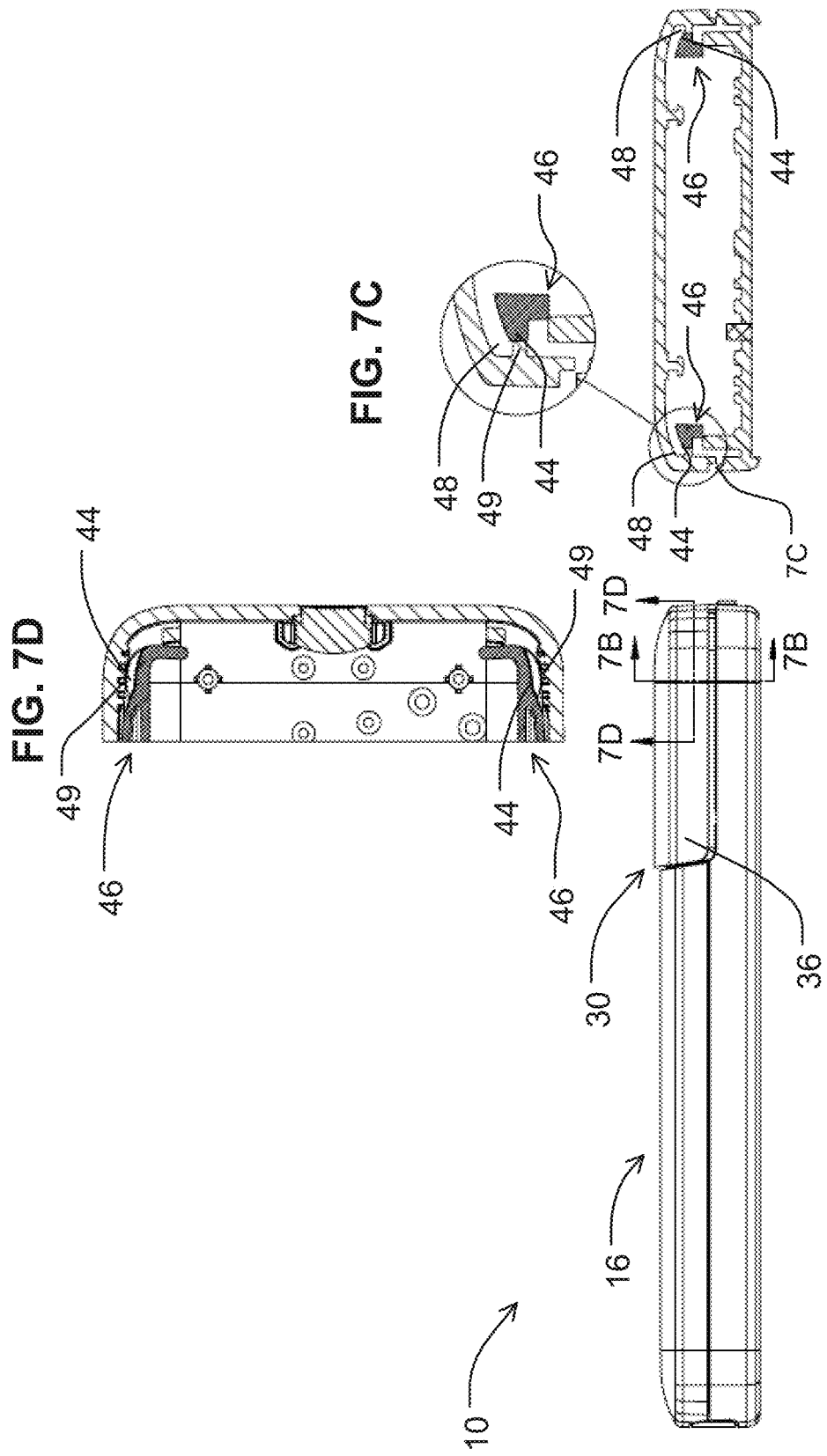

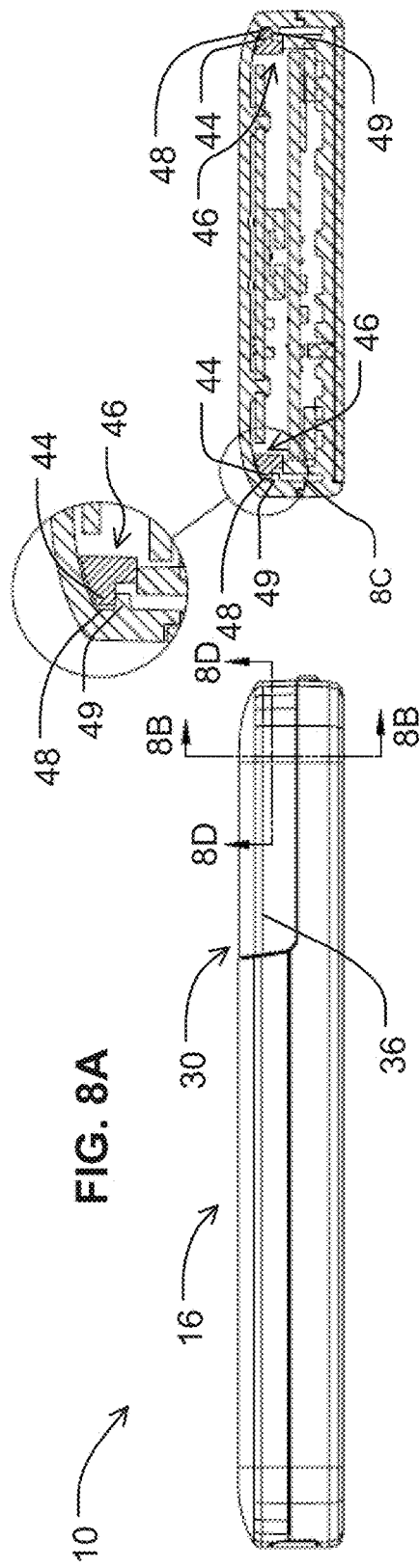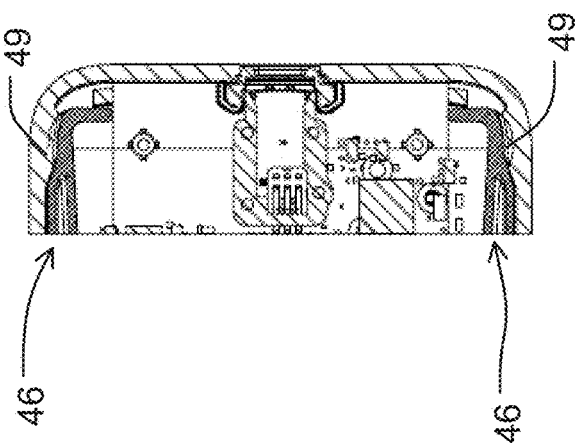

DIAGNOSTIC MEDICAL DEVICE AND METHODS OF USE THEREOF

TECHNICAL FIELD

The present disclosure relates to handheld electronic devices, and more particularly to diagnostic (fluid testing) medical devices.

BACKGROUND INFORMATION

Medical devices include diagnostic devices to determine a medical condition of a patient or other person. Diagnostic medical devices include fluid testing medical devices, which may be used to test bodily fluids of a person. One such diagnostic medical device is a blood glucose meter, which is used as a diagnostic device to determine blood glucose levels of a person having diabetes mellitus.

Blood glucose meters use a test strip that receives a blood sample from a person when placed thereon. The blood glucose meter includes a test strip port to receive the test strip. The test strip includes electrical contacts that are electrically coupled to the meter when the test strip is inserted into the meter. The meter may then determine a blood glucose level by measuring electrical current passed through the electrical contacts of the strip, and provide a determination of the glucose concentration level in the person's blood with an algorithm.

As may be appreciated, a person may have to measure their blood glucose level at various times during a day. As such, the blood glucose meter typically remains with the person. Unfortunately, the meter may be stored or otherwise placed in environments where solid (e.g. dirt) and liquid (e.g. water) debris may enter the test strip port, which may damage the blood glucose meter from proper operation.

It also may be appreciated that a person may have to measure their blood glucose level at night. As such, if surrounding artificial light is not present, it may become difficult to properly place the test strip in the test strip port.

SUMMARY

The present disclosure provides medical devices, particularly diagnostic (fluid testing) medical devices which make use of a test strip to test bodily fluid of a body, particularly that of a person or animal. More particularly, the diagnostic medical devices may be blood glucose meters, which are used as diagnostic devices to a determine blood glucose level of a person or animal having diabetes mellitus.

The diagnostic (fluid testing) medical devices disclosed herein include a test strip port having a test strip port receptacle to receive the test strip. The test strip port may be lighted to assist in proper placement of a test strip in the test strip port at night or otherwise low light conditions. The test strip port may also be protected from egress of solid particulate as well as liquid.

In certain embodiments, a medical device to test bodily fluid may comprise a light emitting source, the light emitting source arranged to emit light inside the medical device; a test strip port, the test strip port having a test strip port receptacle to receive a test strip; and the light emitting source and the test strip port arranged such that, when the light emitting source emits light, at least a portion of the light emitted from the light emitting source is redirected inside the medical device to provide redirected light inside the medical device, and at least a portion of the redirected light lights the test strip port from inside the medical device in a manner than the redirected light is visible outside the test strip port.

In certain embodiments, the test strip port may include a light guide comprising a light guide annular ring defining a light guide annular ring opening, the light guide annular ring arranged such that, when a test strip is received into the test strip port receptacle, the test strip extends through the light guide annular ring opening; and the light guide is arranged to receive light emitted from the light emitting source and redirect at least a portion of the light from the light emitting source towards the light guide annular ring to light the light guide annular ring from inside the medical device. In certain embodiments, the light guide is translucent or transparent.

In certain embodiments, the light guide may be formed from a thermoplastic polymer composition. In certain embodiments, the thermoplastic polymer composition may include at least one translucent polymer and/or at least one transparent polymer. In certain embodiments, the thermoplastic polymer composition may include at least one of polycarbonate, polyurethane, polystyrene and polymethyl methacrylate.

In certain embodiments, the medical device to test bodily fluid may further comprise an outer cover which is detachable from the medical device and reattachable to the medical device, and the test strip port may be fastened to the outer cover. In certain embodiments, the light guide of the test strip port may be fastened to the outer cover.

In certain embodiments, the test strip port may include a test strip connector, the test strip connector including electrical contacts which electrically couple with the test strip, and the light guide may form a pocket with the outer cover which receives a portion of the test strip connector.

In certain embodiments, the light emitting source may be arranged such that, when a test strip is received into the test strip port receptacle, the light from the light emitting source is aimed substantially transverse to a longitudinal axis of the test strip and towards the test strip.

In certain embodiments, the light guide may be arranged to redirect at least a portion of the light from the light emitting source approximately ninety degrees towards the light guide annular ring such that the redirected light travels substantially parallel to the longitudinal axis of the test strip.

In certain embodiments, the test strip port may further comprise a seal which inhibits ingress of at least one of solid particulate and water into the test strip port receptacle.

In certain embodiments, the seal may provide an ingress protection rating of IP22 when tested in accordance with International Standard IEC 60529:1989+A1:1999(E) of the International Electrotechnical Commission.

In certain embodiments, the seal may include a closure flap which extends over at least a portion of the test strip port receptacle.

In certain embodiments, the test strip port may include a light guide comprising a light guide annular ring defining a light guide annular ring opening, the light guide annular ring arranged such that, when a test strip is received into the test strip port receptacle, the test strip extends through the light guide annular ring opening, and the light guide may be arranged to receive light emitted from the light emitting source and redirect at least a portion of the light from the light emitting source towards the light guide annular ring to light the light guide annular ring from inside the medical device, the seal closure flap may extend over at least a portion of the light guide annular ring opening to inhibit the ingress of at least one of the solid particulate and the water into the test strip port receptacle.

In certain embodiments, the seal may comprise a seal annular ring defining a seal annular ring opening, the seal annular ring arranged such that, when a test strip is received into the test strip port receptacle, the test strip extends through the seal annular ring opening.

In certain embodiments, the seal may be formed from an elastomeric polymer composition. The elastomeric polymer composition may include at least one translucent polymer and/or at least one transparent polymer, and the elastomeric polymer composition may include at least one elastomer. The at least one elastomer may be a (silicone) rubber. In certain embodiments, the seal may be translucent or transparent.

The present disclosure also provides a handheld electronic device comprising a main body, a cover engageable to the main body by engagement of a snap-fit connection and disengageable from the main body by disengagement of the snap-fit connection, the snap-fit connection engageable by translational motion of the cover relative to the main body, and the snap-fit connection disengageable by rotational motion of the cover relative to the main body, while the snap-fit connection is not disengageable by translational motion of the cover relative to the main body.

In certain embodiments, the main body comprises a center axis and at least two resilient cantilevered arms, and the at least two resilient cantilevered arms are arranged to move towards and away from the center axis.

In certain embodiments, the at least two resilient cantilevered arms are arranged to move towards each other during engagement of the snap-fit connection.

In certain embodiments, the at least two resilient cantilevered arms each include at least one engagement tab, the cover includes at least two engagement tab receptacles, and each of the at least two engagement tab receptacles is configured to receive one of the engagement tabs.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein:

FIG. 6A is a side view of the medical device of FIG. 1 before the test module is attached to the main body of the medical device;

FIG. 6B is cross-sectional end view of the medical device of FIG. 6A taken along line 6B-6B of FIG. 6A;

FIG. 6C is an enlarged cross-sectional end view of the portion of the medical device within circle 6C of FIG. 6B;

FIG. 7A is a side view of the medical device of FIG. 1 while the test module is being attached to the main body of the medical device;

FIG. 7B is cross-sectional end view of the medical device of FIG. 7A taken along line 7B-7B of FIG. 7A;

FIG. 7C is an enlarged cross-sectional view of the portion of the medical device within circle 7C of FIG. 7B;

FIG. 7D is partial cross-sectional plan view of the medical device of FIG. 7A taken along line 7D-7D of FIG. 7A;

FIG. 8A is a side view of the medical device of FIG. 1 after the test module is attached to the main body of the medical device;

FIG. 8B is cross-sectional end view of the medical device of FIG. 8A taken along line 8B-8B of FIG. 8A;

FIG. 8C is an enlarged cross-sectional view of the portion of the medical device within circle 8C of FIG. 8B;

FIG. 8D is partial cross-sectional plan view of the medical device of FIG. 8A taken along line 8D-8D of FIG. 8A;

DETAILED DESCRIPTION

Figure 2:
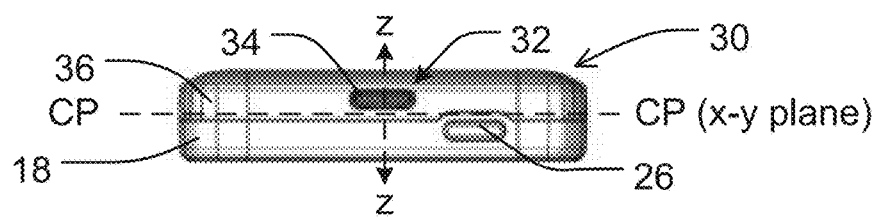
FIG. 2 is a top end view of the medical device of FIG. 1.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

By way of brief introduction, the present disclosure discloses medical devices, particularly diagnostic (fluid testing) medical devices which make use of a test strip to test bodily fluid of a person or animal. More particularly, the diagnostic medical devices may be blood glucose meters, which are used as diagnostic devices to a determine blood glucose level of a person or animal having diabetes mellitus.

Figure 3:
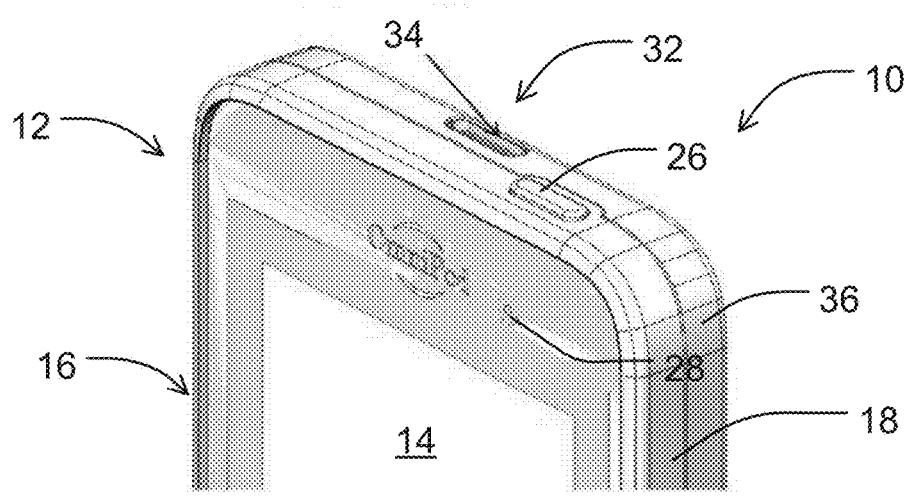
FIG. 3 is a partial perspective view of the medical device of FIG. 1.
Figure 4A:
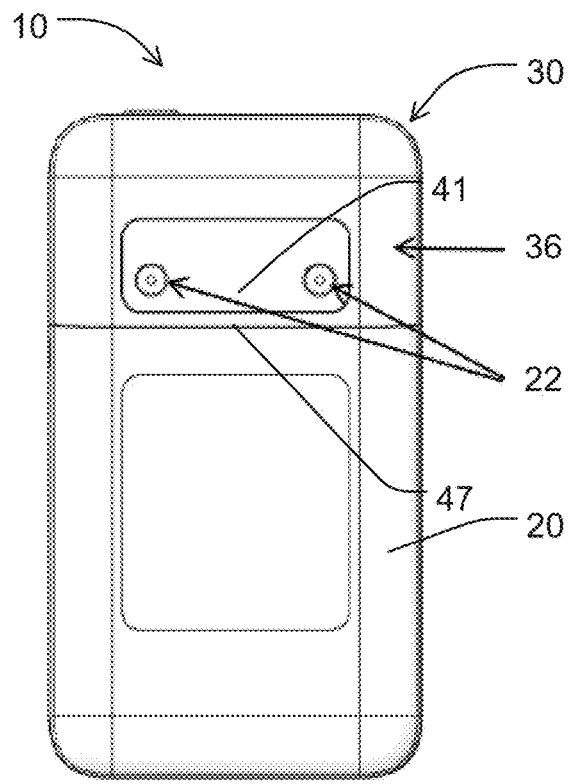
FIG. 4A is a rear (plan) view of the medical device of FIG. 1 with a test module.
Figure 4B:
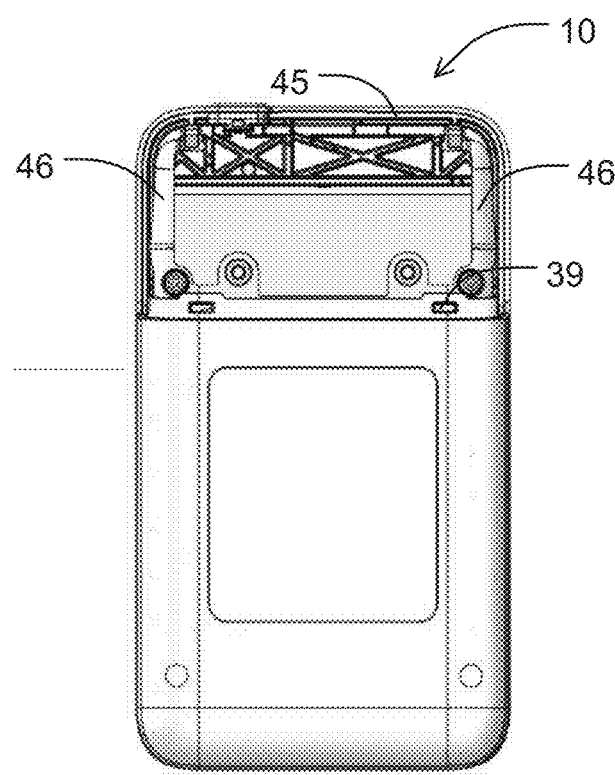
FIG. 4B is a rear (plan) view of the medical device of FIG. 1 without the test module.
Figure 5:
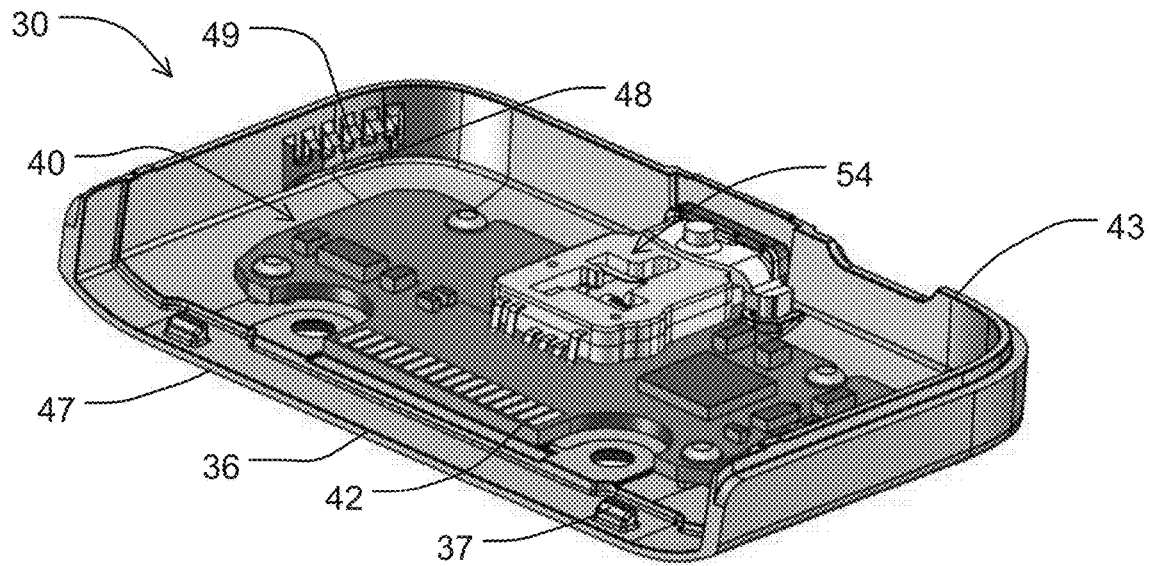
FIG. 5 is an inner perspective view of the test module.

Referring now to the drawings, particularly FIGS. 1-5, there is shown a handheld, electronic, diagnostic (fluid testing) medical device 10, and more particularly a blood glucose meter. As shown, device 10 includes a test strip port 32. As best shown in FIGS. 2-3, test strip port 32 comprises a test strip receptacle 34 to receive a disposable test strip 2 therein (see e.g. FIG. 17). More particularly test strip 2 may be a blood glucose test strip. While medical device 10 may be referred to in particular embodiments herein as a blood glucose meter, the disclosure should not be understood as being limited to blood glucose meters.

Blood glucose meter 10 includes comprises a main body 12. Among other features, main body 12 includes a visual output display panel 14 to display test results.

Main body 12 also includes an enclosure 16 which contains the visual display 14. Enclosure 16 comprises a front housing 18 and a rear housing 20 which provide a housing to protect at least a portion of the main body electronic components contained in the blood glucose meter 10.

Blood glucose meter 10 also includes a removable/detachable and replaceable/reattachable test module 30 which includes the test strip port 32. However, the configuration of the test module 30 and main body 12, and more particularly the following assembly/latching mechanism, may inhibit disassembly/unlatching of the test module 30 by a patient, or other individual/person unauthorized for such removal.

As shown, test module 30 may be mechanically fastened to the main body, particularly by two mechanical fasteners 22, which may particularly comprise threaded fasteners such as screws.

Test module 30 comprises a test module cover 36 to which electronic components 40 of the test module 30 are fastened, which includes at least one printed circuit board.

Figure 1:
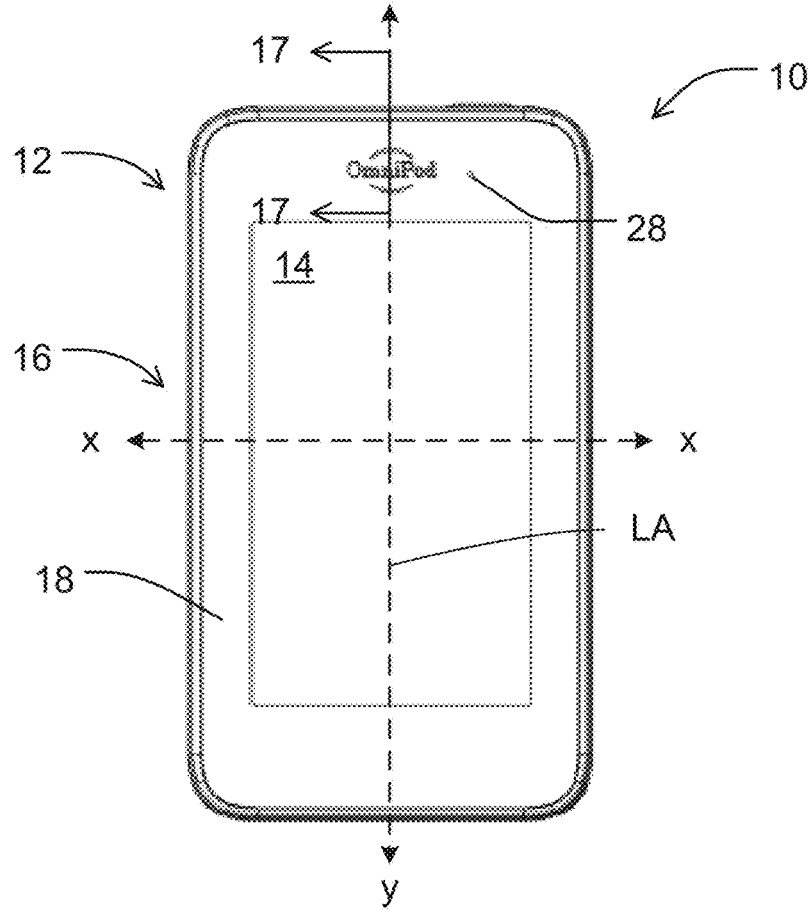
FIG. 1 is a front (plan) view of a medical device according to the present disclosure.

Referring now to FIGS. 6A-8D, the test module 30 may be assembled to the main body 12 with a snap-fit connection by being pressed onto the main body 12, particularly with an assembly force F being applied to the test module 30 transverse to a Cartesian plane CP (parallel with the z-axis) of the main body 12, which may be understood as the x-y reference plane of the Cartesian x, y, z coordinate system (shown in FIGS. 1 and 2).

More particularly, in addition to the use of separate mechanical fasteners 22, test module 30 may also be detachably fastened to main body 12 by a positive mechanical engagement which provides the snap-fit connection. As shown in FIGS. 6A-6C, the positive mechanical engagement may be created by two opposing engagement tabs 44 provided on the lateral outer sides of resilient cantilevered arms 46 of the main body 12, which enter two opposing mating engagement tab receptacles 48, respectively, formed in the cover 36.

During assembly, as shown in FIGS. 7A-7D, and more particularly FIG. 7C, each engagement tab 44 of resilient cantilevered arms 46 bears against an inwardly directed opposing engagement tab 49 of test module cover 36, respectively forcing each cantilevered arm 46 to move inwards from an initial first position (as shown in FIG. 6C) and deflect with elastic deformation towards one another, which inward deflection is biased by the resiliency thereof. More particularly, each cantilevered arm 46 may rotate about the z-axis in the x-y (Cartesian) plane, with each arm moving predominately in the x direction towards the center of the main body 12.

As shown in FIG. 7C, once each cantilevered arm 46 moves to a second position at which the arm 46 deflects inwards a sufficient distance to enable the engagement tabs 44 of each arm 46 to clear the opposing engagement tab 49 of test module cover 36, and enter engagement tab receptacles 48 provided by the test module cover 36, the resiliency of each cantilevered arms 46 may then return each cantilevered arm 46 to its first position as shown in FIGS. 8A-8D, and more particularly FIG. 8C. More particularly, as each engagement tab 44 enters the engagement tab receptacle 48 formed in the test module cover 36, the cantilevered arms 46 rotate outwards to form the positive mechanical engagement and complete assembly of the overlap snap fit connection.

Once assembled, transversely extending peripheral lip 43 and ribs 37 (FIG. 5) of the test module 30 may positively mechanically engage within a mating transverse peripheral groove 45 and rib receptacles 39 (transverse to the x-y plane) of the main body 12, respectively, to inhibit the test module 30 from sliding off the main body 12 along the x-y plane.

As set forth above, the test module 30 may be initially secured by mechanical fasteners 22. However, the mechanical fasteners 22 may be removed in the field. To thwart disassembly of test module 30 in the absence of mechanical fasteners 22, as also explained above, the test module 30 is first configured to inhibit being slid off the main body 12 along the x-y plane. Furthermore, the positive mechanical engagement formed between the main body 12 and test module 30 inhibits the test module 30 from being separated transverse to the x-y plane.

Figure 9A:
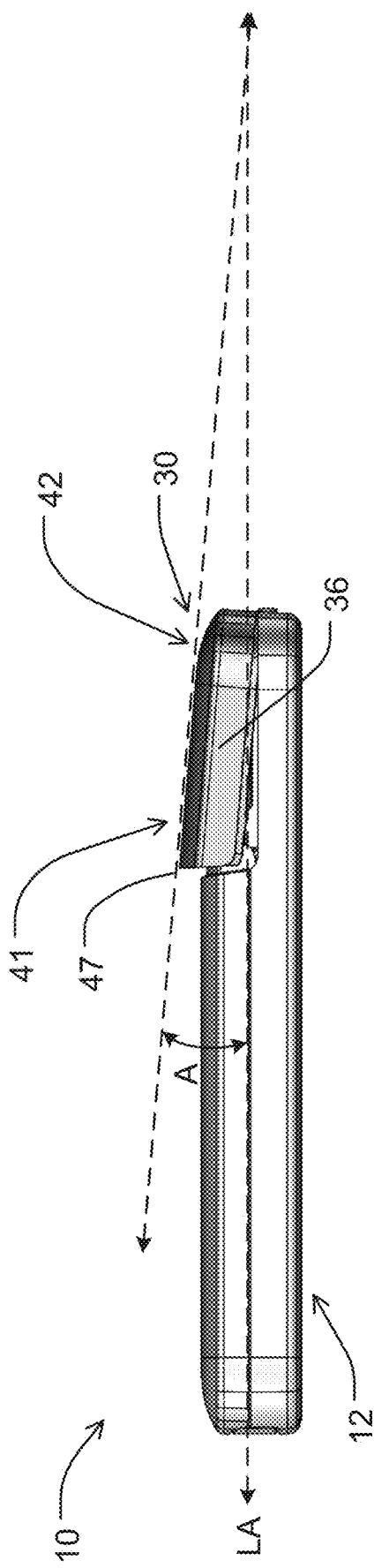
FIG. 9A is a side view of the medical device of FIG. 1 during removal of the test module where the test module is rotated at an angle A of 5 degrees relative to the x-y plane and longitudinal axis LA.
Figure 9B:
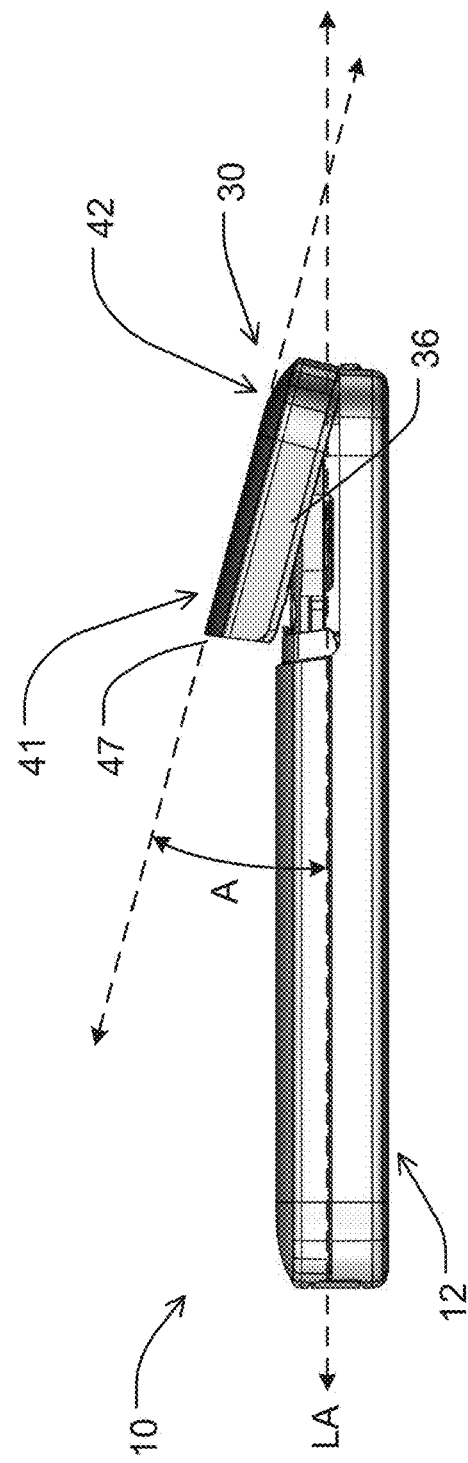
FIG. 9B is a side view of the medical device of FIG. 1 during removal of the test module where the test module is rotated at an angle A of 15 degrees relative to the x-y plane and longitudinal axis LA.
Figure 10:
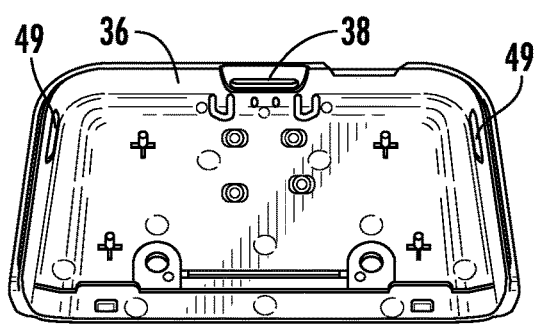
FIG. 10 is an inner view of a cover of the test module of the medical device of FIG. 1 before assembly of the electronic components with the cover.
Figure 11:
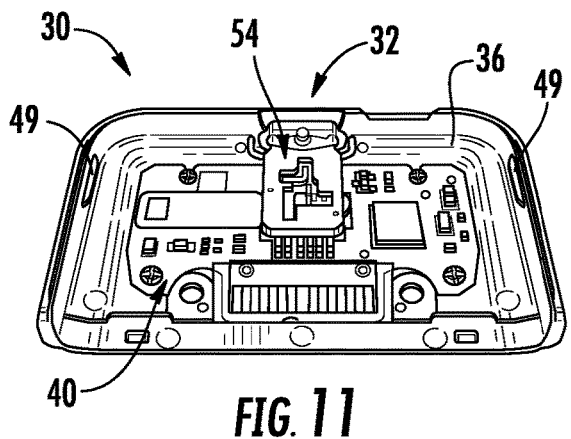
FIG. 11 an inner view of the test module of the medical device of FIG. 1 after assembly of the electronic components with the cover.

Referring now to FIGS. 9A-9B, in order to disassemble test module 30 from the main body 12 after the removal of mechanical fasteners 22, the test module 30 may be rotated relative to the main body 12. More particularly, the test module 30 may be rotated about an axis transverse to the longitudinal axis LA (e.g. x-axis), which is shown further as a center axis, particularly by lifting laterally extending medial edge 47 of test module cover 36. In such manner, a medial region 41 of the test module 30 may be lifted relative to a peripheral region 42 of the test module 30. As the medial region 41 of the test module 30 is raised, such may cause each engagement tabs 44 on the lateral outer sides of resilient cantilevered arms 46 of the main body 12 to once again bear against inwardly directed opposing engagement tab 49 of test module cover 36, respectively forcing each cantilevered arm 46 to cantilever inwards, forcing each cantilevered arm 46 to deflect inwards with elastic deformation towards one another, which is biased by the resiliency thereof. Once each cantilevered arm 46 deflects inwards a sufficient distance to enable the engagement tabs 44 to clear engagement tabs 49 and exit engagement tab receptacles 48 formed in cover 36, the test module 30 is passively released and the resiliency of each cantilevered arms 46 may then return each cantilevered arm 46 to its first position.

The configuration of the test module 30 and main body 12, and more particularly the foregoing disassembly mechanism, is configured to passively release the test module 30 when the test module 30 is rotated at an angle A of 5-30 degrees relative to the longitudinal axis LA, and more particularly 10-20 degrees relative to the longitudinal axis LA.

Now, to further thwart undesirable disassembly of the test module 30, as the medial region 41 of the test module 30 is lifted relative to a peripheral region 42 of the test module 30, the force required to lift the medial region increases (due to increasing resistance of the positive mechanical engagement) as the angle A increases, until the test module 30 is passively released. In light of such, to a person untrained in disassembly of the test module 30, the increase in force to lift the medial region 41 may give an impression that the test module 30 may break if lifted in a manner as set forth above, causing attempted disassembly to be abandoned. However, no portion of the main body 12 or test module 30 is intended to break.

From the foregoing description, a medical device 10 is provided in which the test module cover 36 is engageable to the main body 12 by engagement of a snap-fit connection and disengageable from the main body 12 by disengagement of the snap-fit connection. More particularly, the snap-fit connection is engageable by translational motion of the test module cover 36 relative to the main body 12, and disengageable by rotational motion of the test module cover 36 relative to the main body 12, while not being disengageable by translational motion of the test module cover 36 relative to the main body 12. It should be understood that medical device 10 may be any electronic device, and not be limited to a medical device.

Furthermore, it should be understood that the main body 12 comprises a center axis, such as the longitudinal axis LA, and the cantilevered arms 46 are arranged to move towards and away from the center axis, particularly during engagement/disengagement of the snap-fit connection. More particularly, the cantilevered arms 46 are arranged to move towards each other, as well as away from each other during engagement/disengagement of the snap-fit connection.

Figure 14:
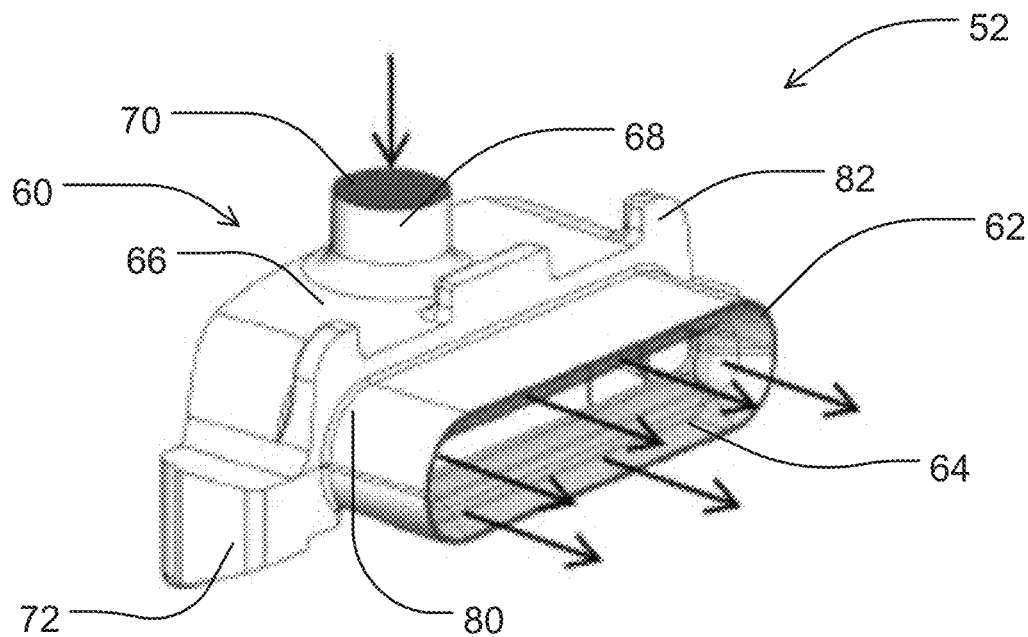
FIG. 14 a perspective view of a light guide of the test module of the medical device of FIG. 1.
Figure 15:
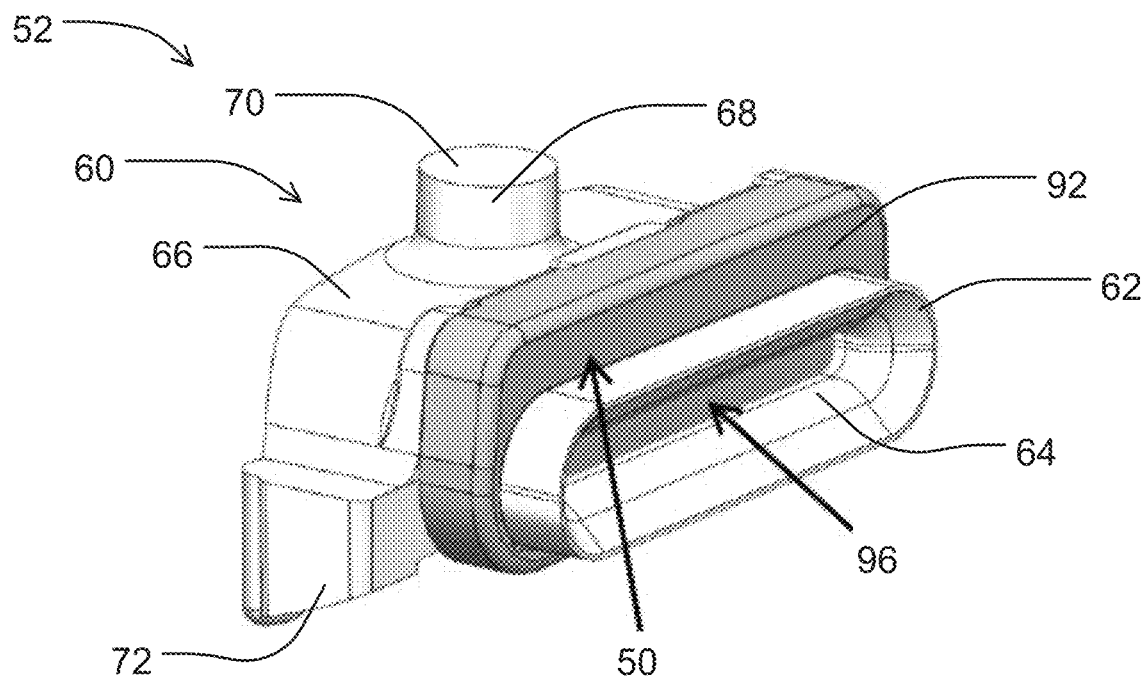
FIG. 15 is a perspective view of the light guide and a seal of the test module of the medical device of FIG. 1.
Figure 16:
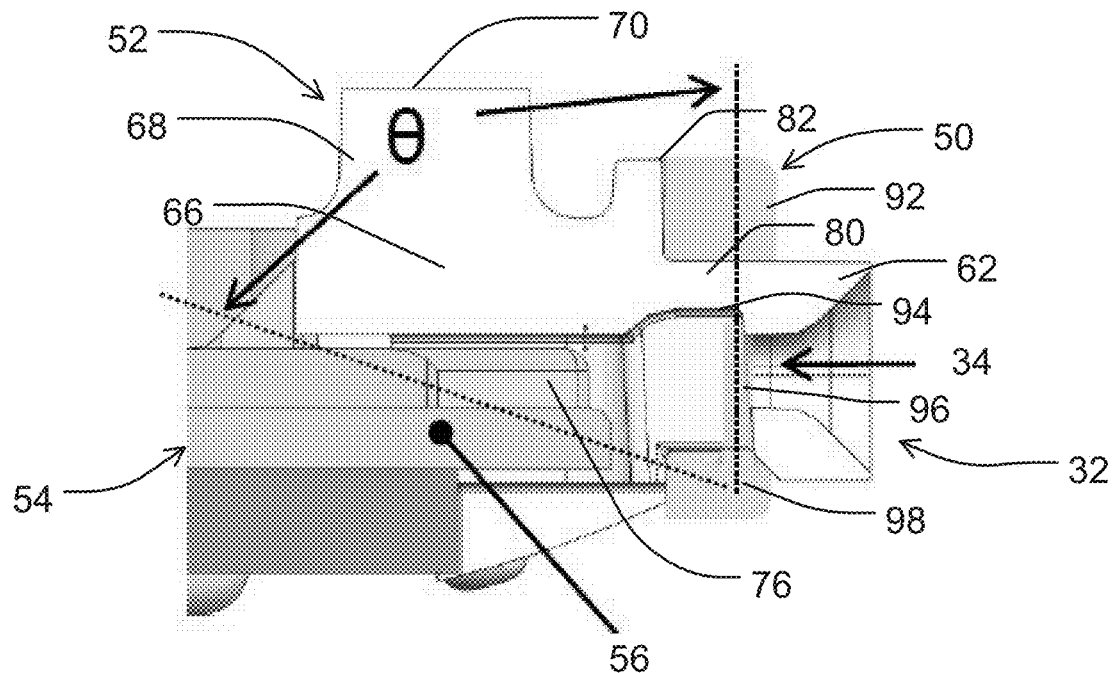
FIG. 16 is a cross-sectional side view of the test module of the medical device of FIG. 5 taken along line 16-16 of FIG. 13 without the cover.

Turning to operation of the test module 30, and FIGS. 10-17, the entrance to the test strip receptacle 34 is provided by a narrow slot (through hole) 38 formed in the test module cover 36. Referring particularly to FIG. 16, the test strip receptacle 34 thereafter extends through seal 50, light guide 52 and into a test strip connector 54, which electrically couples test strip 2 to the electronic components 40 of the test module 30. Once a test strip 2 is inserted within test strip receptacle 34 and properly seated therein, and blood is placed thereon, the blood glucose meter 10 may then determine a blood glucose level by measuring electrical current passed through the electrical contacts of the test strip 2 in a known manner, and provide a determination of the glucose concentration level in the blood.

Figure 17:
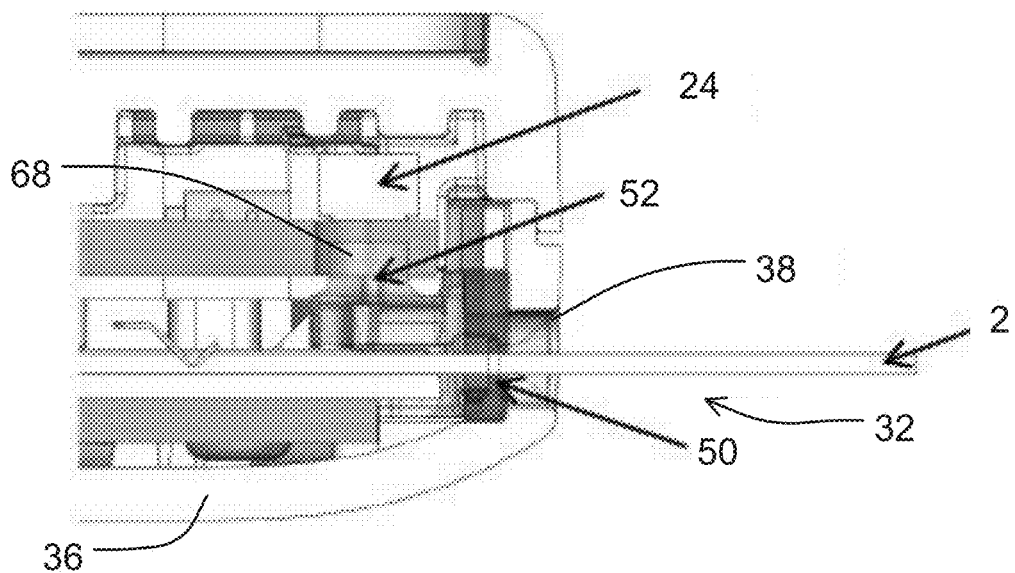
FIG. 17 is a cross-sectional side view of the medical device of FIG. 1 taken along line 17-17 of FIG. 1 with a test strip inserted in the test strip port.

In order to light the test strip port 32 to assist in proper placement of a test strip 2 in the test strip port 32 at night or otherwise low light conditions, light guide 52 receives light from a light emitting source 24 of the blood glucose meter 12 which may be located in the main body 12 (see FIG. 17). Light emitting source 24 may comprise at least one light emitting diode (InGaN, water clear lens, viewing angle 120°/20.5) which emits white (visible) light in a wavelength of 390-700 nm (or frequency range of 430-770 THz) and a luminous intensity in a range of 200-900 millicandela, and more particularly 400-700 millicandela, when tested in accordance with CIE127-2007 ($I_F$=5 mA) standards.

As best shown by FIGS. 14-15, light guide 52 includes a U-shaped section 60 and an oblong annular ring section 62 defining a slot (through hole) 64. As shown, U-shaped section 60 includes a horizontal center span 66 disposed between two spaced apart vertical stanchions 72 which are transverse to the center span 66. Center span 66 includes a centrally disposed cylindrical light receiving post 68 having a planar, circular light receiving surface 70 arranged to receive light from the light emitting source 24 of the main body 12.

Figure 12:
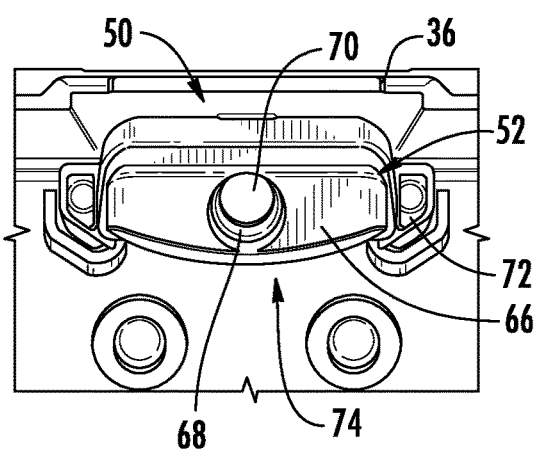
FIG. 12 is a close-up inner view of the test module of FIG. 11 without the electronic components.
Figure 13:
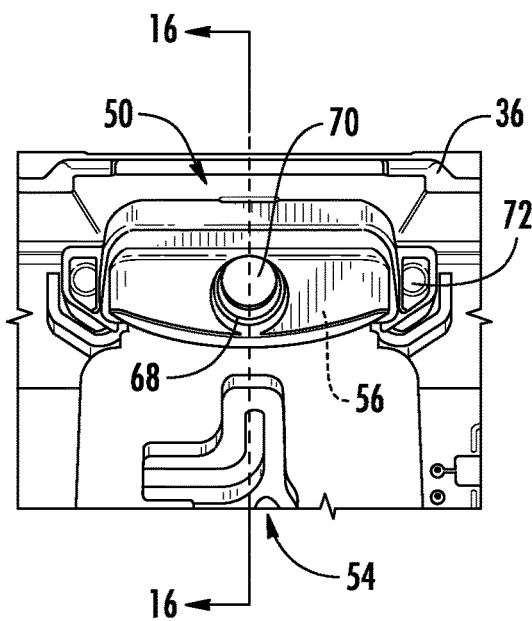
FIG. 13 is close-up inner view of the test module of FIG. 11.

As shown by FIG. 12-13, the vertical stanchions 72 of the U-shaped section 60 are fastened to the inner surface of test module cover 36, particularly by adhesive. The center span 66 and the stanchions 72 form a recess pocket 74 which contains an end lip portion 56 of test strip connector 54. Together, the center span 66 of the U-shaped section 60 of the light guide 52 and the end lip portion 56 of test strip connector 54 define a portion of the test strip receptacle 34, including a slot 76 therebetween to accommodate test strip 2 as it extends through slot 38 in the test module cover 36, slot 64 in the oblong annular ring section 62 of the light guide 52 and completely into test strip connector 54.

In order to transmit light, light guide 52 is formed of a light transmissive polymer composition. As used herein, a light transmissive polymer composition may be characterized as providing integral transmission of at least 60% of incident light in the visible spectrum (about 400-700 nm wavelength), and more preferably at least 70% of incident light in the visible spectrum, and even more preferably, at least 80% or 90% of incident light in the visible spectrum. A light transmissive polymer composition may be optically translucent and, more preferably, an optically transparent. The light transmissive polymer composition may be a thermoplastic polymer composition which is suitable for injection molding. The thermoplastic light transmissive polymer composition may comprise at least one transparent polymer such as polycarbonate, polyurethane, polystyrene and polymethyl methacrylate.

With the foregoing arrangement, the light emitting source 24 is arranged to emit light inside the medical device 10. In addition, the light emitting source 24 and the test strip port 32 are arranged such that, when the light emitting source 24 emits light, at least a portion of the light emitted from the light emitting source 24 is redirected inside the medical device 10 to provide redirected light inside the medical device 10, and at least a portion of the redirected light lights the test strip port 32 from inside the medical device 10.

More particularly, the light guide 52 is arranged to receive light emitted from the light emitting source 24 and redirect at least a portion of the light from the light emitting source 24 towards the light guide annular ring 62 to light the light guide annular ring 62 from inside the medical device 10.

More particularly, the light emitting source 24 is arranged such that, when a test strip 2 is received into the test strip port receptacle 34, the light from the light emitting source 24 is aimed substantially transverse to a longitudinal axis of the test strip 2 and towards the test strip 2. The light guide 52 is arranged to redirect at least a portion of the light from the light emitting source 24 approximately ninety degrees towards the light guide annular ring 62 such that the redirected light travels substantially parallel to the longitudinal axis of the test strip 2.

When light is emitted from light emitting source 24 into light receiving post 68 of light guide 52, light guide 52 is configured such that the light from the oblong annular ring section 62 of the light guide 52 will be emitted in the form of annular ring around the test strip 2, which may be oriented substantially parallel with the longitudinal axis of the test strip 2 upon insertion of the test strip 2 into the test strip port 32.

While blood glucose meter 10 may be configured to automatically light the test strip port 32 in response to receiving a test strip 2 therein, blood glucose meter 10 may also be configured to light test strip port 32 in response to manual push button activation, such as by pushing activation (on/off) button 26 as shown in FIGS. 2 and 3. To save power, the blood glucose meter 10 may include an ambient light sensor 28 to disable such functionally when ambient light is above a predetermined level.

While visible (white) light may be preferred to light the test strip 2, light emitting source 24 may be configured to emit various individual colors of the electromagnetic spectrum. For example, the light emitting source 24 may emit red (620-700 nm), yellow (570-590 nm) or green (495-565 nm) light as an indicator of port status (e.g. green is ready for use, yellow is not ready for use and red is to report an error), or the light may blink to remind the patient to test their blood glucose level.

Test strip port 32 may also be protected from egress of solid particulate as well as liquid by seal 50. Similar to light guide 52, seal 50 includes an oblong annular ring section 92 defining a slot (through hole) 94. Oblong annular ring section 92 is disposed on an intermediate section 80 of the light guide 52 disposed between a shoulder 82 of the U-shaped section 60, and the oblong annular ring section 62. Oblong annular ring section 92 forms a seal against the shoulder 82 of the U-shaped section 60 and the inner surface of test module cover 36 surrounding slot 38 formed in the test module cover 36. In this manner, external debris is inhibited from entering test strip port 32 between seal 52 and test module cover 36.

Oblong annular ring section 92 further includes an elastically deformable U-shaped entrance door flap 96 which is in a closed position when test strip 2 is not within the test strip port 32, and which may rest against (i.e. be in connect with the inner side of oblong annular ring section 62 of light guide 52. At this time, the entrance door flap 96 is in a closed position which substantially closes slot 64 of the light guide 52 to inhibit external debris from entering test strip port 32, and more particularly inhibits debris from entering the test strip receptacle 34 beyond slot 64 in the oblong annular ring section 62 of the light guide 52.

When test strip 2 is inserted within test strip port 32, elastically deformable entrance door flap 96 deforms elastically inward, particularly along a hinge portion 98, upon being contacted by test strip 2 to open slot 64 in the oblong annular ring section 62 of the light guide 52 and correspondingly open slot 94 in the oblong annular ring section 92 of seal 50. Entrance door flap 96 may rotate at an angle θ in a range of, for example of 60 to 90 degrees.

Seal 52 may be particularly formed of an elastomeric polymer composition. As used herein, an elastomeric polymer composition may be characterized as a composition that has an elongation at 23° C. of at least 100%, and which, after being stretched to twice its original length and being held at such for one minute, may recover in a range of 50% to 100% within one minute after release from the stress. More particularly, the an elastomeric polymer composition may recover in a range of 75% to 100% within one minute after release from the stress, and even more particularly recover in a range of 90% to 100% within one minute after release from the stress. The elastomeric polymer composition may be a composition with a Tg below room temperature and which is at most, 50% crystalline (i.e., the material contains an amorphous phase of 50% or greater, up to 100% amorphous phase). The elastomeric polymer composition may comprise a thermoplastic polymer composition which is suitable for injection molding. The elastomeric polymer composition may comprise at least one thermoplastic elastomer, such as styrene block polymers, such as styrene block copolymers (e.g. styrene-butadiene copolymer) and styrene block terpolymers (e.g. styrene-butadiene-styrene terpolymer, styrene-ethylene/butylene-styrene terpolymer, styrene-ethylene/propylene-styrene terpolymer); polyolefin blends (e.g. polypropylene and ethylene-propylene-diene monomer rubber, polypropylene and nitrile rubber, ethylene-propylene rubber); elastomeric alloys such as melt-processable rubbers and thermoplastic vulcanizates; polyolefins; polyurethanes; polyesters; and rubbers such as natural rubber, neoprene rubber, acrylic rubber, butadiene rubber, butyl rubber, ethylene-propylene rubber, ethylene propylene diene monomer rubber, fluorocarbon rubber, isoprene rubber, nitrile rubber, polyurethane rubber and silicone rubber.

The seal 52 may also be formed of a rigid polymer composition, particularly where the hinge portion 98 may be configured as a living hinge. Example materials include polypropylene or acrylonitrile-butadiene-styrene.

Furthermore, the elastomeric polymer composition of seal 52 may also be a light transmissive polymer composition. As used herein, a light transmissive polymer composition may be characterized as providing integral transmission of at least 60% of incident light in the visible spectrum (about 400-700 nm wavelength), and more preferably at least 70% of incident light in the visible spectrum, and even more preferably, at least 80% or 90% of incident light in the visible spectrum. A light transmissive polymer composition may be optically translucent and, more preferably, an optically transparent.

With the foregoing constriction, seal 50 of the test strip port 32 of blood glucose meter 10 may passively seal to inhibit external debris, liquid (e.g. water) and solid (e.g. dirt), from entering the test strip port. More particularly, test strip port 32 may be sealed to meet IP22 fluid and particulate ingress requirements for home use medical products per International Electrotechnical Commission International Standard IEC 60529:1989+A1:1999(E), which is incorporated herein by reference.

The IP Code, International Protection Marking or IEC standard 60529, sometimes interpreted as Ingress Protection Marking or IP Rating, classifies and rates the degree of protection provided against intrusion (body parts such as hands and fingers), dust, accidental contact, and water by mechanical casings and electrical enclosures. It is published by the International Electrotechnical Commission (IEC) as noted above.

For example, an electrical socket rated IP22 is protected against insertion of fingers and will not be damaged or become unsafe during a specified test in which it is exposed to vertically or nearly vertically dripping water. The first digit indicates the level of protection that the enclosure provides against ingress of solid foreign objects. A level of 2 corresponds to the enclosure providing protection against ingress of objects greater than 12.5 mm, which is effective against fingers or similar objects. The second digit indicates the level of protection that the enclosure provides against harmful ingress of water. A level of 2 corresponds to the enclosure providing protection against ingress of dripping water when tilted up to 15 degrees (i.e. vertically dripping water shall have no harmful effect when the enclosure is tilted at an angle up to 15° from its normal position). The enclosure is tested for 10 minutes, with a water equivalent to 3 mm rainfall per minute.

Furthermore, when light is emitted from light emitting source 24 into light receiving post 68 of light guide 52, light guide 52 is configured such that light will be transmitted and directed into the oblong annular ring section 92 of seal 50 such that light from the oblong annular ring section 92 of the seal 50 will be emitted in the form of annular ring around the test strip 2.

Moreover, when light is emitted from light emitting source 24 into light receiving post 68 of light guide 52, light guide 52 is configured such that light will be transmitted and directed into the door flap 96 of seal 50 such that light will be emitted from the door flap 96 of the seal 50.

In addition to the foregoing, medical device 10 may also provide protection against electrostatic discharge (ESD). For example, medical device 10 may comply with International Standard IEC 60601-2-24:2012, as tested per IEC 61000-4-2: 2008, incorporated by reference, (Electromagnetic compatibility (EMC)—Part 4: Testing and measurement techniques—Section 2: Electrostatic Discharge Immunity Test) at a level of +/−8 kV contact discharge and +/−15 Kv air discharge.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

LIST OF REFERENCE CHARACTERS 2 test strip
10 medical device
12 main body
14 visual display
16 main body enclosure
18 front housing
20 rear housing
22 mechanical fasteners
24 light emitting source
26 light emitting source activation (on/off) push button
28 ambient light sensor
30 test module
32 test strip port
34 test strip receptacle
36 test module cover
37 ribs
38 test module cover slot
39 rib receptacles
40 test module electronic components
41 medial region
42 peripheral region
43 transverse lip
44 engagement tab
45 transverse groove
46 cantilevered arm
47 medial edge
48 engagement tab receptacle
49 engagement tab
50 seal
52 light guide
54 test strip connector
56 test strip connector end portion
60 U-shaped section
62 oblong annular ring section
64 oblong annular ring section slot
66 center span
68 light receiving post
70 light receiving surface
72 stanchion
74 recess pocket
76 slot
80 intermediate section
82 shoulder
92 oblong annular ring section
94 oblong annular ring section slot
96 entrance door flap
98 hinge portion
A angle

What is claimed is:

1. A medical device to test bodily fluid, the device comprising:
a light emitting source, the light emitting source arranged to emit light inside the medical device;
a test strip port, the test strip port comprising:
a light guide and a test strip port receptacle to receive a test strip; and
a seal which inhibits ingress of at least one of solid particulate and water into the test strip port receptacle;
the light emitting source and the light guide of the test strip port arranged such that, in an absence of the test strip, when the light emitting source emits light, at least a portion of the light emitted from the light emitting source is redirected by the light guide inside the medical device to provide redirected light inside the medical device, and at least a portion of the redirected light lights the test strip port from inside the medical device in a manner than the redirected light is visible outside the test strip port;
wherein the light guide comprises a light guide annular ring defining a light guide annular ring opening, the light guide annular ring arranged such that, when a test strip is received into the test strip port receptacle, the test strip extends through the light guide annular ring opening;
wherein the light guide annular ring extends though the seal; and
wherein the light guide is arranged to receive light emitted from the light emitting source and redirect at least a portion of the light from the light emitting source towards the light guide annular ring to light the light guide annular ring from inside the medical device.

2. The device of claim 1 wherein: the light guide is formed from a polymer composition.

3. The device of claim 1 wherein: the light guide is translucent or transparent.

4. The device of claim 1 further comprising:
an outer cover which is detachable from the medical device and reattachable to the medical device; and
the test strip port is fastened to the outer cover.

5. The device of claim 4 wherein: the light guide of the test strip port is fastened to the outer cover.

6. The device of claim 5 wherein:
the test strip port includes a test strip connector, the test strip connector including electrical contacts which electrically couple with the test strip; and
the light guide forms a pocket with the outer cover which receives a portion of the test strip connector.

7. The device of claim 4 wherein:
the test strip port includes a test strip connector, the test strip connector including electrical contacts which electrically couple with the test strip; and
the light guide forms a pocket with the outer cover which receives a portion of the test strip connector.

8. The device of claim 5 wherein: the light guide is arranged to redirect at least a portion of the light from the light emitting source approximately ninety degrees towards the light guide annular ring such that the redirected light travels substantially parallel to a longitudinal axis of the test strip.

9. The device of claim 1 wherein: the light emitting source is configured to emit a particular color of light indicative of a use status of the test strip port.

10. The device of claim 1 wherein: the light emitting source is arranged such that, when a test strip is received into the test strip port receptacle, the light from the light emitting source is aimed substantially transverse to a longitudinal axis of the test strip and towards the test strip.

11. The device of claim 1 wherein: the light guide is arranged to redirect at least a portion of the light from the light emitting source approximately ninety degrees towards the light guide annular ring such that the redirected light travels substantially parallel to a longitudinal axis of the test strip.

12. The device of claim 1 wherein: the seal includes a closure flap which extends over at least a portion of the test strip port receptacle.

13. The device of claim 12 wherein: the closure flap extends over at least a portion of the light guide annular ring opening to inhibit the ingress of at least one of the solid particulate and the water into the test strip port receptacle.

14. The device of claim 1 wherein the light guide annular ring defines a slot, and wherein when a test strip is received into the test strip port receptacle, the test strip extends through the slot.

15. The device of claim 1 wherein: the seal is formed from a polymer composition.

16. The device of claim 1 wherein: the seal is translucent or transparent.

17. The device of claim 1, wherein the seal comprises a seal annular ring, and wherein the light guide annular ring extends though the seal annular ring.

* * * * *